United States Patent
Mall et al.

(10) Patent No.: US 6,235,932 B1
(45) Date of Patent: May 22, 2001

(54) PROCESS FOR PREPARATION OF ADIPIC ACID

(75) Inventors: Sanjib Mall; Sreeramagiri Siva Kumar, both of Pune (IN)

(73) Assignee: Chemintel (India) Private Ltd., Gujarat (IN)

( * ) Notice: Subject to any disclaimer, the term of this patent is extended or adjusted under 35 U.S.C. 154(b) by 0 days.

(21) Appl. No.: 09/392,460

(22) Filed: Sep. 9, 1999

(30) Foreign Application Priority Data

Jun. 18, 1999 (IN) ............................................. 454/BOM/99

(51) Int. Cl.⁷ .................................................. C07C 51/31
(52) U.S. Cl. .............................................................. 562/543
(58) Field of Search .................................................. 562/543

(56) References Cited

U.S. PATENT DOCUMENTS

| | | | |
|---|---|---|---|
| 2,223,493 | 12/1940 | Loder | 260/537 |
| 2,589,648 | 3/1952 | Wadsworth | 260/533 |
| 3,231,608 | 1/1966 | Kollar | 260/533 |
| 3,390,174 | 6/1968 | Schulz et al. | 260/533 |
| 4,032,569 | 6/1977 | Onopchenko et al. | 260/533 C |
| 4,202,797 | 5/1980 | Jones | 252/413 |
| 4,263,453 | 4/1981 | Schulz et al. | 562/543 |
| 4,902,827 | 2/1990 | Steinmetz et al. | 562/543 |
| 5,166,421 | 11/1992 | Bruner | 562/522 |
| 5,218,144 | 6/1993 | Atadan | 562/517 |
| 5,221,800 | 6/1993 | Park et al. | 562/543 |
| 5,321,155 | 6/1994 | Drinkard et al. | 562/524 |
| 5,321,157 | 6/1994 | Kollar | 562/543 |
| 5,455,375 | 10/1995 | Ide et al. | 562/590 |
| 5,463,119 | 10/1995 | Kollar | 562/543 |
| 5,547,905 | 8/1996 | Kulsrestha et al. | 502/66 |
| 5,587,511 | 12/1996 | Salzburg et al. | 562/513 |
| 5,710,325 | 1/1998 | Bruner et al. | 562/517 |
| 5,756,837 | 5/1998 | Costantini et al. | 562/543 |
| 5,780,683 | 7/1998 | Greene et al. | 568/358 |
| 5,824,819 | 10/1998 | Dassel et al. | 562/529 |
| 5,922,908 | 7/1999 | Dassel et al. | 562/543 |

FOREIGN PATENT DOCUMENTS

| | | |
|---|---|---|
| 1 304 855 | 1/1973 | (GB) . |
| 94/07834 | 4/1994 | (WO) . |
| 96/03365 | 2/1996 | (WO) . |

OTHER PUBLICATIONS

Aldrich Catalog Handbook of Fine Chemicals, p. 32, 1993.*
Article entitled "One–Step Oxidation of Cyclohexane to Adipic Acid" by G.N. Kulsrestha et al. J. Chem. Tech. Biotechnol. 1991, 50, 57–65.
Article entitled "Synthesis of Adipic Acid by single Stage Oxidation of Cyclohexane" by Kyugo Tanaka, Papers presented before the division of Petroleum Chemistry, Inc. American Chemicals Society, 1974.
Article entitled "Adipic Acid By Single Stage" by Kyugo Tanaka, Hydrocarbon Processing, Nov., 1974 pp 114–120.

* cited by examiner

*Primary Examiner*—Howard C. Lee
*Assistant Examiner*—Leigh C. Maier
(74) *Attorney, Agent, or Firm*—Michael D. Bednarek; Shaw Pittman

(57) ABSTRACT

The present invention relates to one-step oxidation process for preparation of cyclohexane to adipic acid, using molecular oxygen, in liquid phase, in the presence of catalyst, containing either cobalt or cobalt and iron. The catalyst is activated outside the reactor and molecular oxygen is used as an oxidant. The use of molecular oxygen as oxidant along with preactivated catalyst in the reactor and also by restricting the conversion of cyclohexane between 20–30% with catalyst in the reactor results in enhanced selectivity to adipic acid. The reaction mixture of cyclohexane and pre-activated catalyst is subjected to oxidation by bubbling pure molecular oxygen while stirring the homogenous mixture while bubbling the oxygen at a predetermined temperature, pressure and space velocity conditions. The product selectivity to form adipic acid is found to be at least 5% better than the maximum attainable using the conventional processes.

6 Claims, 2 Drawing Sheets

Figure 1:
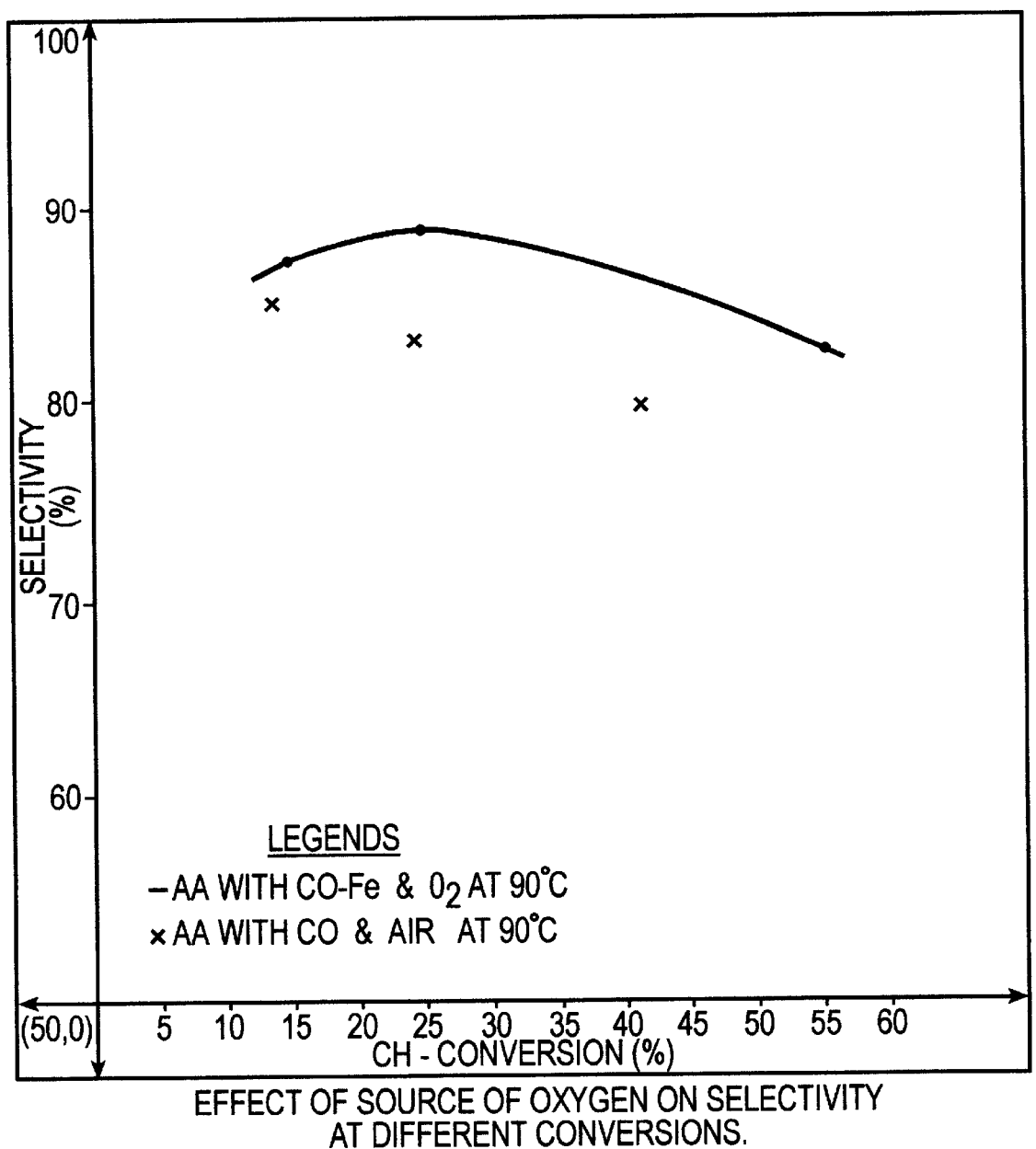

EFFECT OF SOURCE OF OXYGEN ON SELECTIVITY
AT DIFFERENT CONVERSIONS.

EFFECT OF SOURCE OF OXYGEN ON SELECTIVITY
AT DIFFERENT CONVERSIONS.

PROCESS FOR PREPARATION OF ADIPIC ACID

The present invention relates to process for the formation of adipic acid from cyclohexane and the adipic acid thus formed.

The invention resides in the use of pure molecular oxygen as an oxidant which results in providing higher selectivity towards the formation of adipic acid.

The object of the invention is to increase the selectivity and the yield of adipic acid from cyclohexane. The product selectivities using the process of the present invention have been found to be at least 5% higher than the maximum attainable using the hitherto known conventional processes. The process of the present invention employs use of preactivated catalyst in the reactor for carrying out the reaction.

BACKGROUND OF THE INVENTION

Adipic acid is widely used in the manufacture of polyesters, polyamides, plasticizers and the like. Conventionally adipic acid is known to be produced by two step oxidation of cyclohexane. In the first step KA oil is produced from cyclohexane by air oxidation which is then oxidized by nitric acid to dicarboxylic acids such as adipic acid, glutaric acid and succinic acid. This process suffers from various disadvantages, especially relating to low conversion per pass of the hydrocarbon in the first step (3–8%), leading to large recycle; use of nitric acid in the second step leading to NOx pollution; and formation of byproducts like lactones which pose difficulties in the downstream use of adipic acid.

In order to overcome drawbacks in the two step oxidation process, one step oxidation of cyclohexane has been tried over the years. Air is used as an oxidant in one step oxidation of cyclohexane. The catalysts mostly used in the oxidation of cyclohexane are cobalt and its mixture with other metals like iron. In the conventional methods, in-situ activation of the catalyst from cobaltous to cobaltic state is carried out with the help of activators like aldehydes and ketones.

The earlier known patents have divulged the use of any oxygen containing gas, however, the known art does not bring-out the differences in selectivity to adipic acid and conversion of CH while using pure oxygen instead of any oxygen containing gas. The prior art has also not been able to achieve a higher selectivity to give better yields using high purity oxygen versus use of air or dilute oxygen as conventionally used.

The direct oxidation of cyclohexane to adipic acid is a process that has attracted much attention on account of the obvious advantages there would be in avoiding the nitric acid oxidation of KA-oil and its associated nitric acid handling activities. Processes that have been proposed for preparing dibasic acids without the use of nitric acid include air oxidation of saturated cyclic hydrocarbons and/or corresponding cyclic ketones and/or-alcohols. For example, U.S. Pat. No. 3,390,174 and British Patent 1,304,855 disclose processes requiring mixtures of two or more of these components. However, many such air oxidation processes are multi-step processes and do not provide the required high yield as well as high selectivity.

Single-step direct air oxidation processes for the production of dibasic acids have also been proposed and used in the prior art. However, previously known one-step processes have been attended by poor selectivities, low production rates, costly separation steps and relatively rapid deactivation of the catalyst during its recycling. For example, U.S. Pat. No. 2,223,493 discloses a process for the oxidation of cyclic hydrocarbons to corresponding diacids, in a liquid phase generally containing acetic acid at a temperature of at least 60° C., using a gas containing oxygen and in the presence of an oxidation catalyst such as cobalt compound. The selectivities reported in this patent are as low as 46 to 49 mole percent. Furthermore, the patent fails to address the issues of recycling the catalyst and the activity which a catalyst that has been recycled one or more times would have.

U.S. Pat. No. 2,589,648 describes a single-step oxidation process wherein acetone is used in the place of acetic acid as solvent.

U.S. Pat. No. 3,231,608 describes a similar process, suggesting that molar ratios of solvent to saturated cyclic hydrocarbon in the range of 1:5:1 to 7:1 (or more) are suitable but that molar ratios below or above this range give unsatisfactory results.

U.S. Pat. No. 4,032,569 teaches a process for converting cyclohexane to adipic acid which involves oxidizing cyclohexane with molecular oxygen in the presence of critical amounts of cobaltic ions, which is mentioned to be in the range of 25 to 150 millimols per mole of cyclohexane charged. Catalyst activation is in situ during the initial induction period. It is observed in this patent that either air or molecular oxygen can be used for the oxidation. No effect of gas phase concentration of oxygen is studied, but, the total pressure is mentioned to be higher than 11 kg/cm$^2$. Adipic acid, glutaric acid and succinic acid are the main products of the reaction with very low concentration of others. The analysis method, however, is not specified.

U.S. Pat. No. 4,263,453 is a continuation of the above work, with a modification in the procedure that water is added to the reaction mixture in the initial stages to enhance the selectivity to adipic acid. It is claimed that the addition of water improves the yield of adipic acid. However the induction period increases several fold thereby decreasing the rate of production severely.

U.S. Pat. No. 4,902,827 discloses a process for the production of adipic acid from cyclohexane in the presence of cobalt and zirconium and/or hafnium catalyst using air.

U.S. Pat. No. 5,221,800 also discloses a process for producing adipic acid from cyclohexane but with intermittent addition of water. It is claimed that water, if present during the induction period, depletes the concentration of free radicals which are so essential for catalyst activation It is shown that water addition after the induction period is more advantageous and results in a selectivity of about 88%. However this selectivity calculation is based only on the identifiable compounds. The true selectivity with all other compounds considered is not given.

U.S. Pat. No. 5,321,157 revisits the cobalt catalysed oxidation. All previous work on one-step oxidation is argued in this patent to be inefficient as they employ low initial concentration of cyclohexane and higher reaction times. They claim that oxidation of high concentrations of cyclohexane at low conversion levels provides advantageous chemical and economic results. Low conversions are achieved by using low concentrations of catalyst. Use of oxygen gas or oxygen containing gas is recommended and the conversions are restricted to below 30%. The product mixture is analysed in gas chromatography after esterification with excess methanol. This is claimed that with this analysis, selectivity of adipic acid is obtained to be about 80 to 88%. In this work also oxygen or any oxygen containing gas is claimed to produce the desired results.

Patent Application WO-A-94/07834 and U.S. Pat. No. 5,463,119 disclose a process which develops the stage for the purification of the final mixture. This treatment consists in separating the diacid formed, by cooling the mixture in order to bring about precipitation of the diacid, and in separating by filtration the diacid from two liquid phases, a non-polar one which is recycled, and a polar one which is also recycled after an optional hydrolysis and a separation of an additional amount of diacid. Furthermore, it provides significant information on removing the aliphatic dibasic acid (preferably as a precipitate collected by filtration or centrifugation) and recycling intermediates, post-oxidation components, and derivatives thereof remaining after removal of the aliphatic dibasic acid.

U.S. Pat. No. 5,756,837 is similar to this patent but discloses a process for recycling a catalyst containing cobalt including treating a reaction mixture obtained during the direct oxidation of cyclohexane to adipic acid by extracting at least some of the glutaric acid and succinic acid which are formed in the reaction.

U.S. Pat. No. 5,547,905, a patent by the same applicant as of the present invention, describes a process for adipic acid production by one-step oxidation in the presence of a novel Co-Fe catalyst. In this patent, a new catalyst activation step is disclosed and use of pure oxygen as oxidant is mentioned. In this work conversion of cyclohexane is taken upto 70% in about 4 to 6 hours. Average selectivity to adipic acid is about 75%. This patent also shows that the Co-Fe catalyst can be used successfully for the oxidation of other hydrocarbon like xylenes, toluenes and cyclopentane to their corresponding dicarboxylic acid.

SUMMARY OF THE INVENTION

The present invention relates to one-step oxidation of cyclohexane to adipic acid, using molecular oxygen, in liquid phase and in the presence of a catalyst, containing either cobalt or cobalt and iron. In the present invention, it is found that by restricting the conversion of cyclohexane between 20 to 30% with catalyst activated outside the reactor and using molecular oxygen as oxidant, the selectivity to adipic acid is enhanced significantly.

The present invention also brings about the advantages of using molecular oxygen as oxidant to achieve better yield and selectivity to adipic acid compared to air.

The process of the present invention highlights that the use of any dilute oxygen results in lower production rates and over-oxidation of cyclohexane thereby reducing the economics of the process.

BRIEF DESCRIPTION OF THE ACCOMPANYING DRAWINGS

FIG. 1 presents a graph highlighting the effect of source of oxygen on selectivity at different conversions.

Figure 2:
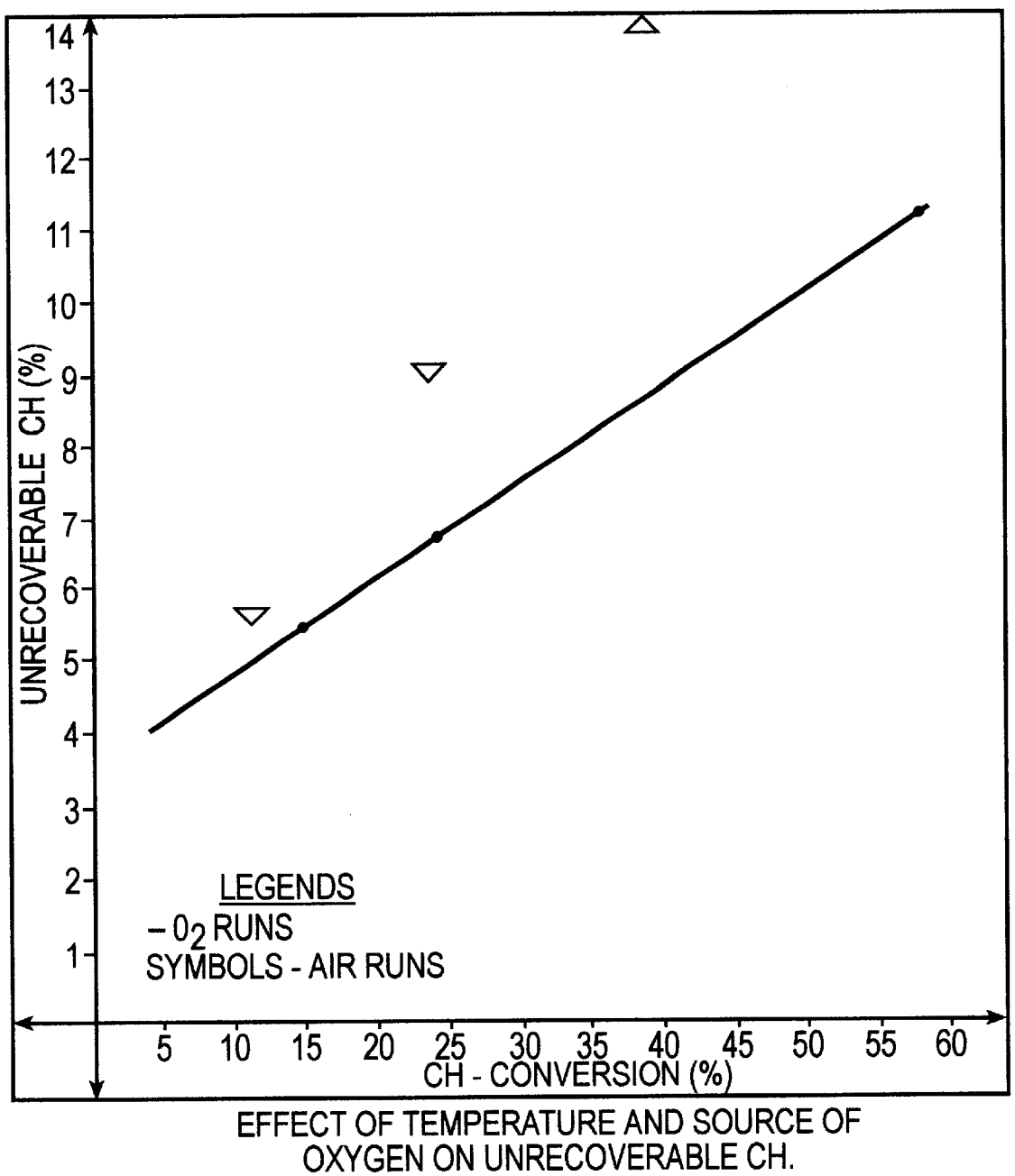

FIG. 2 depicts a graph highlighting the effect of temperature and source of oxygen on unrecoverable CH.

DETAILED DESCRIPTION OF THE INVENTION

The present invention relates to a process for the preparation of adipic acid by one step oxidation of cyclohexane. The main embodiment of the present invention resides in the enhanced selectivity towards adipic acid as a result of the process employed for the conversion of cyclohexane.

The present invention relates to a process for producing adipic acid from cyclohexane using pre-activated catalyst system and molecular oxygen for oxidation which results in an increase in the production rate as the induction period is eliminated. Further, in an another embodiment of the present invention, the activation of the catalyst is carried out at atmospheric pressure outside the reactor which reduces the capital cost. In yet another embodiment of the present invention selectivity to adipic acid is greatly enhanced by restricting the conversion of cyclohexane to below 30%. In an another embodiment of the invention it is shown that the intermediate formation as well as by product formation is greatly reduced by the process of the present invention, i.e., the concentration of intermediates like cyclohexanol is insignificant, at the same time the formation of the side products like succinic acid is also very less when molecular oxygen is used instead of any oxygen containing gas like air.

The process of the present invention uses molecular oxygen instead of air or dilute oxygen showing a profound beneficial effect on selectivity, restricts the conversion to below 30% so that formation of succinic acid and glutaric acid is reduced and uses pre-activated Co or Co-Fe catalyst.

The oxidation reaction for the process of the present invention is carried out in a gas-liquid stirred reactor. The reaction mixture is in liquid phase through which the gases are bubbled at space velocities in the range of 15 to 50 $hr^{-1}$. The liquid is well stirred so as to ensure that the liquid phase is homogeneous and also that above 90% of the oxygen sent in is consumed in the reactor by recirculating the gas bubbles several times in the reactor. The oxygen gas coming out of the liquid is diluted with nitrogen gas such that the gas phase concentration of oxygen is less than 5%. The out going gases are cooled to condense the organic compounds being carried away. The condensed organics are returned to the reactor. The gas is vented out after measuring the oxygen and carbon dioxide concentrations. The reactor is provided with external heating coil for heating the reaction liquid and internal cooling coils to maintain the liquid temperature at the desired level. The reaction can be carried out in batch mode or continuous mode in this reactor.

The process of the present invention employs use of salts of Co or Co-Fe as a catalyst where the acid part of the catalyst is selected from the group consisting of acetate, propionate, naphthenate, adipate and phthalate.

Prior to use in the process for the oxidation of cyclohexane to adipic acid, the catalyst, with desired amounts of iron is activated to cobaltic-ferric form by bubbling oxygen through a solution of cobaltous-iron acetate in acetic acid, in the presence of ketones such as methyl ethyl ketone or cyclohexanone or aldehydes like acetaldehyde as promoters, at temperature in the range between 90–130° C. and at atmospheric pressure. The catalyst should be present in the ratio of 0.01 to 0.1 (mole ratio) to cyclohexane for the reaction to proceed optimally. The activated catalyst is thereafter stored at room temperature.

The process of the present invention employs use of solvent and cyclohexane in the ratio of 1.5:1 to 6.5:1 by weight. The catalyst concentration is varied in the range from 0.01 to 0.1 molar ratio with cyclohexane. Activator is ranging from 0.5 to 1.0 molar ratio with catalyst.

Oxygen flow rate is such that at least 90% oxygen is consumed in the reaction system. For the range of parameters studied this translates to a space velocity of 15 to 50 $hr^{-1}$. Temperature is varied in the range of 90 to 110° C. Pressure of the system is maintained in the range of 15 to 35 $kg/cm^2$ or 200 to 500 lb. per sq. inch.

According to process of the present invention, the oxidation of cyclohexane is carried out at desired temperature and pressure, in the presence of an activated catalyst. The activated catalyst in acetic acid and cyclohexane is prepared earlier and transferred to the reactor. The reactor is pressurized to desired pressure using nitrogen. The temperature of the reaction mixture is gradually raised to the desired temperature and maintained constant Oxygen is bubbled through the reaction mixture during the entire reaction process. The oxidation reaction time is measured from the moment the liquid temperature reaches the desired value.

The reaction mixture at the end of the oxidation contains, among others, acetic acid, cyclohexane, water, cobalt catalyst and all the oxidation products such as adipic acid, glutaric acid, succinic acid reaction intermediates and esters of diacids. In the product recovery section, the oxidation products are separated from acetic acid the solvent, cyclohexane, water and catalyst. This is achieved by first distilling off the volatiles from the reaction mixture. After all the acetic acid is removed, the residue is a mixture of oxidation products and catalyst Co-Fe acetate. The separation of these two is achieved by extracting the oxidation products with a suitable solvent like acetone or methyl ethyl ketone. The catalyst is filtered off and dried to be reused. The oxidation products are recovered from acetone by evaporating acetone and drying. This product mixture contains adipic acid and other organic compounds. These are analyzed by Gas chromatography and the selectivity of cyclohexane converted to adipic acid is measured. Pure adipic acid is obtained from the mixture in the purification section in repeated crystallizations from solvents like water, acetic acid, methanol and the like.

Acetic acid recovered from the reaction section contains water produced during the oxidation reaction. The water is removed by distillation and the pure acetic acid is recycled to the reactor.

The oxidation products are in solid state when recovered by the above said procedure. These are derivated and analysed in gas chromatography as liquid samples to obtain the product distribution. This is achieved by forming methyl esters of the products and dissolving them in ether. This liquid solution is injected in gas chromatography with FID detector.

There are two methods of forming the methyl esters. One is by adding excess methanol to the product mixture in the presence of a catalyst (the methanol method) and the other is by esterification with diazo methane (the diazo method). From literature it can be noted that methanol method is most widely used. However this method has several drawbacks. Firstly the esterification is never complete. Therefore there are monoesters formed which have different retention times in the gas chromatography than the di-methyl esters. This leads to an error in the analysis. In order to overcome this, strong acid catalysts like boron trifloride are used. However, methanol method converts lot of intermediates and esters formed in the reaction mixture into di-methyl esters. For example a product like monocyclohexyl adipate, a stable compound formed during the oxidation by the reaction of cyclohexanol (an intermediate) and adipic acid, is converted to di-methyl adipate which is same as that formed by methylation of free adipic acid formed in the reaction. Thus both these different compounds give a peak at the same retention time and appear as same compound in the gas chromatogram. Therefore, the product distribution is not correctly obtained by this method leading to an erroneous over-estimate of the selectivity to adipic acid.

The other method is the diazo method which ensures that the esterification is complete. There are no strong acid catalysts and this reaction is essentially irreversible. More importantly the esters, of the di-acids with reaction intermediates like cyclohexanol, remain unaltered. These are not converted to di-methyl esters of adipic acid and thus appear as separate peaks in the gas chromatogram.

A comparative analysis of results from diazo method and methanol method is clearly brought out in the following table which shows the weight percentage of various components in the oxidation product in a typical run. As evident from this table, the ester of adipic acid and alcohol intermediates is separately estimated in the diazo method where as by the methanol method they are all clubbed in adipic acid peak. As a result the diazo method estimates the adipic acid weight fraction as 75% while the methanol method estimates 92%.

The prior art is known to have used the methanol method and reports selectivity in the range of 80 to 88%. But as illustrated here the actual product distribution is likely to be very different.

TABLE 1

Effect of method of esterification on the estimated product distribution

| Compound | Weight Percent | |
|---|---|---|
| | Methanol method | Diazo method |
| Adipic acid | 92.1 | 76.1 |
| Glutaric acid | 3.5 | 3.4 |
| Succinic acid | 0.6 | 0.6 |
| Esters of adipic acid | 2.7 | 10.6 |
| Esters of glutaric acid | 0.5 | 1.5 |
| Esters of succinic acid | 0.3 | 1.3 |
| Other intermediates | 0.3 | 6.5 |

To attain concrete results, the diazo method has been used to analyse the products of the present invention.

The process of the present invention provides higher selectivity towards oxidation. The percentage of glutaric acid and succinic acid formed in the present work is much less than the values hitherto reported by the conventional processes. At the same time the intermediates like cyclohexanone and cyclohexanol are not present in the subject product mixture. It means that the process of the present invention provides a faster rate of conversion of compounds which are precursors to adipic acid but slower rate of oxidation of cyclohexane to acids which form after adipic acid, thereby maximizing the conversion to adipic acid.

As mentioned above, in all the earlier works on single step oxidation the source of oxygen or the concentration of oxygen in the gas phase is considered unimportant. In most of the cases air or dilute oxygen is used as the oxidant for experiments but any oxygen containing gas is claimed for the oxidation. None of these conventional works address the effect of the oxygen concentration in gas phase on the selectivity, and fail to underline the significance of using pure oxygen. Results of the present invention clearly indicate that there is a significant effect of gas concentration of oxygen on the cyclohexane oxidation. FIG. 1 and Table 2 summarizes these results and show the selectivity to adipic acid at different conversions at different temperature using oxygen or air as source of oxygen. As can be seen from this graph (FIG. 1), at all the conversions the selectivity with oxygen as oxidant is much higher than that using air. This difference is as high as 8% at the optimum conversion.

TABLE 2

EFFECT OF OXIDANT ON SELECTIVITY

| SR No | Catalyst | Oxidant | Cyclohexane Conversion (%) | Selectivity to adipic acid (%) | Unrecoverable Cyclohexane (%) |
|---|---|---|---|---|---|
| 1. | Cobalt acetate | Air | 13 | 57.3 | 5.7 |
| 2. | Cobalt acetate | Air | 24 | 60.4 | 9.0 |
| 3. | Cobalt + iron acetate | Air | 42 | 64.2 | 13.9 |
| 4. | Cobalt + iron acetate | Oxygen | 15 | 65.6 | 5.5 |
| 5. | Cobalt + iron acetate | Oxygen | 25 | 70.0 | 6.7 |
| 6. | Cobalt acetate | Oxygen | 21 | 72.1 | 8.1 |
| 7. | Cobalt + iron acetate | Oxygen | 55 | 64.1 | 10.8 |

Column six of the Table 2 show the percentage of cyclohexane that goes towards glutaric and succinic acids and their derivatives (termed unrecoverable cyclohexane) at different conversions using oxygen or air as oxidants. This is the cyclohexane that can not be recovered and recycled in the reaction system to further produce adipic acid, i.e., this is the cyclohexane that has been over-oxidized even beyond adipic acid. This data again shows that air oxidation results in large unrecoverable cyclohexane that is greater loss of the precious reactant as compared to oxygen. So a process using molecular oxygen has better economics and should be used as oxidant for single step oxidation of Cyclohexane to adipic acid.

Accordingly the present invention relates to a process for preparation of adipic acid from cyclohexane comprising
forming a reaction mixture in liquid phase of cyclohexane and preactivated catalyst in a gas liquid stirred reactor;
bubbling pure molecular oxygen in the said liquid phase reaction mixture at a space velocity of 15–50 hr$^{-1}$, at a temperature in the range of 90–110° C. and a pressure in the range of 15–35 Kg/cm$^2$ while stirring the said reaction mixture so as to ensure that the said liquid phase reaction mixture is homogenous and also that above 90% of the pure oxygen is consumed in the reactor by recirculating the gas bubbles several times in the said reactor thereby forming a reaction mixture including oxidation products, cyclohexane, water and catalyst;
diluting the unreacted oxygen gas coming out of the said homogenous liquid with nitrogen such that the gas phase concentration of oxygen is less than 5%;
removing the volatile products from the said resultant mixture by distillation to form a residue comprising catalyst and the oxidation products;
extracting the oxidation products from the said residue using suitable solvents such as acetone, methyl ethyl ketone and the like, filtering off and drying the separated catalyst for recycling the same;
recovering the said oxidation products by evaporating the solvent and drying;
repeatedly recrystallising the said oxidation products to separate pure adipic acid, using solvents like water, acetic acid, methanol and the like, from unrecoverable cyclohexane;
recycling the unreacted cyclohexane.
In yet other embodiment the present invention relates to a process for preparation of adipic acid from cyclohexane comprising
forming a reaction mixture in liquid phase of cyclohexane and preactivated catalyst in a gas liquid stirred reactor;
bubbling pure molecular oxygen in the said liquid phase reaction mixture at a space velocity of 15–50 hr$^{-1}$, at a temperature in the range of 90–110° C. and a pressure in the range of 15–35 Kg/cm$^2$ while stirring the said reaction mixture so as to ensure that the said liquid phase reaction mixture is homogenous and also that above 90% of the pure oxygen is consumed in the reactor by recirculating the gas bubbles several times in the said reactor thereby forming a reaction mixture including oxidation products, cyclohexane, water and catalyst;
diluting the unreacted oxygen gas coming out of the said homogenous liquid with nitrogen such that the gas phase concentration of oxygen is less than 5% followed by cooling to condense she organic compounds being carried away along with the unreacted oxygen gas, and, recycling the condensed organic compounds;
removing the volatile products from the said resultant mixture by distillation to form a residue comprising catalyst and the oxidation products;
extracting the oxidation products from the said residue using suitable solvents such as acetone, methyl ethyl ketone and the like, filtering off and drying the separated catalyst for recycling the same;
recovering the said oxidation products by evaporating the solvent and drying;
repeatedly recrystallising the said oxidation products to separate pure adipic acid, using solvents like water, acetic acid, methanol and the like, from unrecoverable cyclohexane;
recycling the unreacted cyclohexane.

EXAMPLES

The present invention can be understood in a better manner with the help of examples wherein the following definitions are used:

Conversion is the percentage of cyclohexane from that charged converted to products.

Selectivity is the ratio of moles of cyclohexane going towards forming the desired product divided by the total moles of cyclohexane reacted.

In the following examples, the end product formed by the process of the present invention has been analysed by diazo method as well as methanol method whereas the conventionally known literature and patents employ methanol method for analysis. The comparative results of both the analysis methods are reproduced herein below.

Example 1

63 g cobalt acetate and 3 g iron acetate are dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurised to 20 kg/cm$^2$ total pressure using nitrogen and heated to 100° C. Oxygen gas (99% pure) is bubbled through the agitated liquid at an hourly space velocity of 35 hr.$^{-1}$ and the reaction is carried out for 120 minutes. The reaction is thereafter cooled and products recovered. Total weight of product recovered is 412 g.

Conversion of cyclohexane is 55%.

Selectivity by diazo method: to adipic acid is 64.1%, glutaric acid 6.7% and succinic acid 2.44%.

Example 2

63 g cobalt acetate and 3 g iron acetate are dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurised to 20 kg/cm² total pressure using nitrogen and heated to 100° C. Oxygen gas (99% pure) is bubbled through the agitated liquid at an hourly space velocity of 35 hr.$^{-1}$ and the reaction is carried out for 120 minutes. The reaction is thereafter cooled and products recovered. Total weight of product recovered is 412 g.

Conversion of cyclohexane is 55%.

Selectivity by methanol method: to adipic acid is 89.1%, glutaric acid 6.7% and succinic acid 1.8%.

Example 3

63 g cobalt acetate and 3 g iron acetate are dissolved in 2060 g acetic acid and activated in the presence of cyclohexanone of about 15 g. The activated catalyst along with acetic acid is mixed with 480 g cyclohexane, and charged to the gas-liquid stirred reactor. The reaction mixture is pressurized to 20 kg/cm² total pressure using nitrogen and heated to 90° C. Oxygen gas (99% pure) is bubbled through the agitated liquid at an hourly space velocity of 20hr$^{-1}$. The reaction is carried out for 120 minutes. The reaction mixture is cooled and products recovered. Total weight of product recovered is 190 g.

Conversion of cyclohexane is 26%.

Selectivity by diazo method: to adipic acid is 69.7%, glutaric acid 3.9% and succinic acid 1.0%.

Example 4

63 g cobalt acetate and 3 g iron acetate are dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 90° C. Oxygen gas (99% pure) is bubbled through the agitated liquid at an hourly space velocity of 20hr$^{-1}$. The reaction is carried out for 120 minutes. The reaction mixture is cooled and products recovered. Total weight of product recovered is 190 g.

Conversion of cyclohexane is 26%.

Selectivity by methanol method: to adipic acid is 89.5%, glutaric acid 3.8%, succinic acid 0.3%.

Example 5

63 g cobalt acetate and 3 g iron acetate are dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 100° C. Air is bubbled through the agitated liquid at an hourly space velocity of 35 hr.$^{-1}$. The reaction is carried out for 500 minutes. The reaction mixture is cooled and products recovered. Total weight of product recovered is 289 g. Conversion of cyclohexane is 43%.

Selectivity by diazo method: to adipic acid is 64.3%; glutaric acid 8.3% and succinic acid 2.34%.

Example 6

63 g cobalt acetate and 3 g iron acetate are dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 100° C. Air is bubbled through the agitated liquid at an hourly space velocity of 35 hr.$^{-1}$. The reaction is carried out for 500 minutes. The reaction mixture is cooled and products recovered. Total weight of product recovered is 289 g. Conversion of cyclohexane is 43%.

Selectivity by methanol method: to adipic acid is 85.3%, glutaric acid 7.8% and succinic acid 2.2%.

Example 7

66 g cobalt acetate is dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 90° C. Air is bubbled through the agitated liquid at an hourly space velocity of 35 hr$^{-1}$. The reaction is carried out for 300 minutes. The reaction mixture is cooled and products recovered. Total weight of product recovered is 187 g. Conversion of cyclohexane is 24%.

Selectivity by diazo method: to adipic acid is 60.4%; glutaric acid 3.9% and succinic acid 0.97%.

Example 8

66 g cobalt acetate is dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 90° C. Air is bubbled through the agitated liquid at an hourly space velocity of 35 hr$^{-1}$. The reaction is carried out for 300 minutes. The reaction mixture is cooled and products recovered. Total weight of product recovered is 187 g. Conversion of cyclohexane is 24%.

Selectivity by methanol method: to adipic acid is 87.9%, glutaric acid 5.6% and succinic acid 1.7%.

Example 9

66 g cobalt acetate is dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 90° C. Oxygen is bubbled through the agitated liquid at an hourly space velocity of 20 hr$^{-1}$. The reaction is carried out for 120 minutes. The reaction mixture is cooled and products recovered. Total weight of product recovered is 142 g. Conversion of cyclohexane is 21%.

Selectivity by diazo method: to adipic acid is 72.1%; glutaric acid 5.0% and succinic acid 0.98%.

Example 10

66 g cobalt acetate is dissolved in 2060 g acetic acid and activated in the presence of cyclohexanone of about 15 g. The activated catalyst along with acetic acid is mixed with 480 g cyclohexane and charged to the gas-liquid stirred reactor. The reaction mixture is pressurized to 20 kg/cm² total pressure using nitrogen and heated to 90° C. Oxygen is bubbled through the agitated liquid at an hourly space velocity of 20 hr$^{-1}$. The reaction is carried out for 120 minutes. The reaction mixture is cooled and products recovered. Total weight of product recovered is 142 g. Conversion of cyclohexane is 21%.

Selectivity by methanol method: to adipic acid is 93.9%, glutaric acid 5.0% and succinic acid 0.56%.

Thus the one-step oxidation of cyclohexane to adipic acid is carried out in the presence of pre-activated catalyst (Co-Fe) using molecular oxygen. Analysis method using esterification by diazomethane of the reaction products provides an accurate picture of the product distribution as compared to methanol method which though widely employed, leads to gross overestimation of the selectivity to adipic acid. Selectivity to adipic acid is obtained to be greater than 90% with oxygen as the oxidant and with pre-activated catalyst when the conversion of Cyclohexane is restricted to 20–30%. Amount of glutaric and succinic acid, the lower homologous molecules formed is less than any of the conventionally known processes. In other words the present invention relates to a process where formation of the cyclohexane unrecoverable is less than any of the earlier works. This greatly improves the economics of the process.

We claim:

1. A process for preparation of adipic acid from cyclohexane consisting essentially of:

forming a reaction mixture in liquid phase of cyclohexane and preactivated catalyst in a gas liquid stirred reactor;

bubbling pure molecular oxygen in the said liquid phase reaction mixture at a space velocity of 15–50 hr$^{-1}$, at a temperature in the range of 90–110° C. and a pressure in the range of 15–35 Kg/cm$^2$ while stirring the said reaction mixture so as to ensure that the said liquid phase reaction mixture is homogenous and also that above 90% of the pure oxygen is consumed in the reactor by recirculating the gas bubbles several times in the said reactor thereby forming a reaction mixture including oxidation products, cyclohexane, water and catalyst;

diluting the unreacted oxygen gas coming out of the said homogenous liquid with nitrogen such that the gas phase concentration of oxygen is less than 5%;

removing the volatile products from the said resultant mixture by distillation to form a residue comprising catalyst and the oxidation products;

extracting the oxidation products from the said residue using methyl ethyl ketone or acetone, filtering off and drying the separated catalyst for recycling the same;

recovering the said oxidation products by evaporating the solvent and drying;

repeatedly recrystallising the said oxidation products to separate pure adipic acid, using solvents selected from the group consisting of water, acetic acid, and methanol, from unrecoverable cyclohexane; and recycling the unreacted cyclohexane.

2. A process for the preparation of adipic acid from cyclohexane as claimed in claim 1, wherein the said preactivated catalyst comprises cobaltic or cobaltic-ferric salts, the acid component of the salt being selected from the group consisting of acetate, propionate, naphthenate, adipate and phthalate.

3. A process for the preparation of adipic acid from cyclohexane as claimed in claim 2, wherein the said catalyst and cyclohexane concentration is varied in the range of 0.01 to 0.1 molar ratio.

4. A process for the preparation of adipic acid from cyclohexane as claimed in claim 1, wherein the said reactor is pressurised to desired pressure using nitrogen.

5. A process for the preparation of adipic acid from cyclohexane as claimed in claim 4, wherein the said reactor is provided with external heating coil for heating the homogenous liquid and internal cooling coils to maintain the liquid temperature at the desired level.

6. A process for preparation of adipic acid from cyclohexane consisting essentially of:

forming a reaction mixture in liquid phase of cyclohexane and preactivated catalyst in a gas liquid stirred reactor;

bubbling pure molecular oxygen in the said liquid phase reaction mixture at a space velocity of 15–50 hr$^{-1}$, at a temperature in the range of 90–110° C. and a pressure in the range of 15–35 Kg/cm$^2$ while stirring the said reaction mixture so as to ensure that the said liquid phase reaction mixture is homogenous and also that above 90% of the pure oxygen is consumed in the reactor by recirculating the gas bubbles several times in the said reactor thereby forming a reaction mixture including oxidation products, cyclohexane, water and catalyst;

diluting the unreacted oxygen gas coming out of the said homogenous liquid with nitrogen such that the gas phase concentration of oxygen is less than 5% followed by cooling to condense the organic compounds being carried away along with the unreacted oxygen gas, and, recycling the condensed organic compounds;

removing the volatile products from the said resultant mixture by distillation to form a residue comprising catalyst and the oxidation products;

extracting the oxidation products from the said residue using methyl ethyl ketone or acetone, filtering off and drying the separated catalyst for recycling the same;

recovering the said oxidation products by evaporating the solvent and drying; repeatedly recrystallising the said oxidation products to separate pure adipic acid, using solvents selected from the group consisting of water, acetic acid, and methanol, from unrecoverable cyclohexane; ad recycling the unreacted cyclohexane.

* * * * *